United States Patent [19]

Logothetis et al.

[11] Patent Number: 5,049,254

[45] Date of Patent: * Sep. 17, 1991

[54] EXHAUST GAS RECIRCULATION SENSOR

[75] Inventors: Eleftherios M. Logothetis, Birmingham; Richard E. Soltis, Redford, both of Mich.

[73] Assignee: Ford Motor Company, Dearborn, Mich.

[ * ] Notice: The portion of the term of this patent subsequent to Mar. 20, 2007 has been disclaimed.

[21] Appl. No.: 55,821

[22] Filed: May 29, 1987

[51] Int. Cl.[5] ............................................. G01N 27/41
[52] U.S. Cl. ..................................... 204/425; 204/426
[58] Field of Search ................................. 204/421–429

[56] References Cited

U.S. PATENT DOCUMENTS

| 4,300,991 | 11/1981 | Chiba et al. | 204/426 |
| 4,487,680 | 12/1984 | Logothetis et al. | 204/426 |
| 4,496,455 | 1/1985 | Linder et al. | 204/425 |
| 4,574,627 | 3/1986 | Sakurai et al. | 204/426 |
| 4,578,171 | 3/1986 | Yamada et al. | 204/426 |
| 4,645,572 | 2/1987 | Nishizawa et al. | 204/425 |
| 4,722,779 | 2/1988 | Yamada et al. | 204/425 |
| 4,765,880 | 8/1988 | Hayakawa et al. | 204/426 |
| 4,769,124 | 9/1988 | Okada et al. | 204/426 |
| 4,909,072 | 3/1990 | Logothetis et al. | 204/426 |

OTHER PUBLICATIONS

"Basic Electrical Engineering", Fitzgerald et al, 2nd ed., 1957, p. 25.

Primary Examiner—T. Tung
Attorney, Agent, or Firm—Peter Abolins; Keith L. Zerschling

[57] ABSTRACT

An electrochemical device and method measures the percentage of exhaust gas for circulation in a combined intake air and exhaust gas mixture of an internal combustion engine. Two electrochemical pump cells and a support structure form a restricted volume in communication through an aperture to an ambient of intake air and exhaust gas mixture. Constant voltage is applied across a first pump cell to cause oxygen molecules inside the volume to be pumped out. A constant voltage across the second pump cell causes dissociation of all $CO_2$ and $H_2O$ molecules inside the volume. Current flowing in the second pump cell is measured, the current being proportional to the percentage of $CO_2$ plus $H_2O$ inside the volume and also proportional to the percentage of $CO_2$ plus $H_2O$ in the combined intake air and exhaust gas mixture.

1 Claim, 4 Drawing Sheets

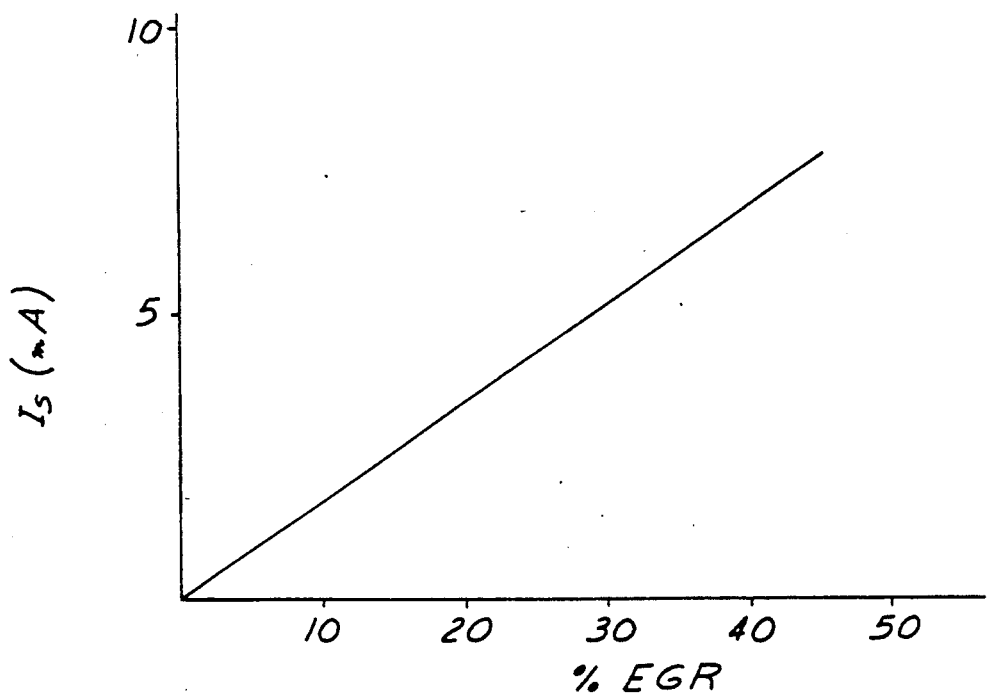
FIG.4
FIG.5
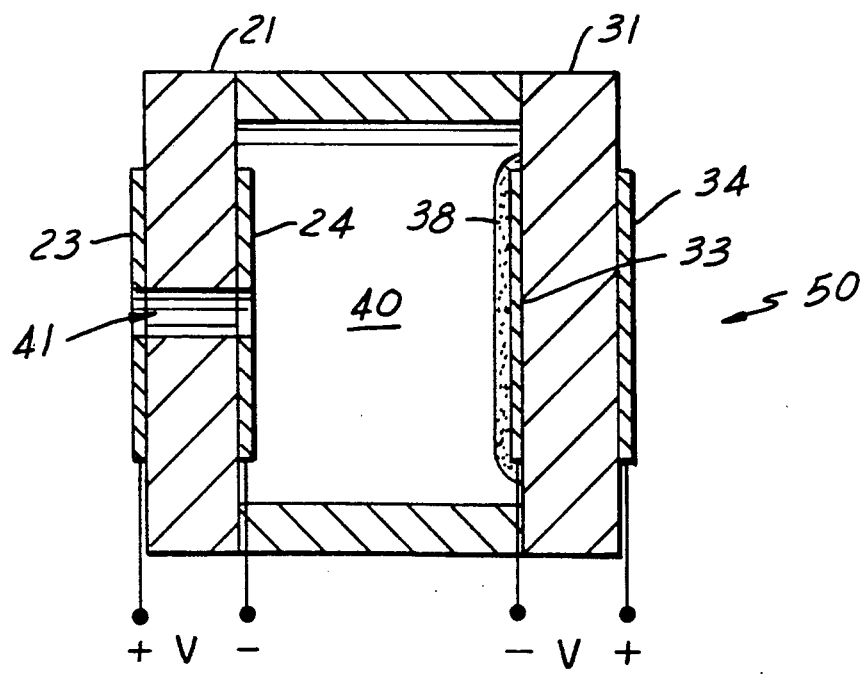

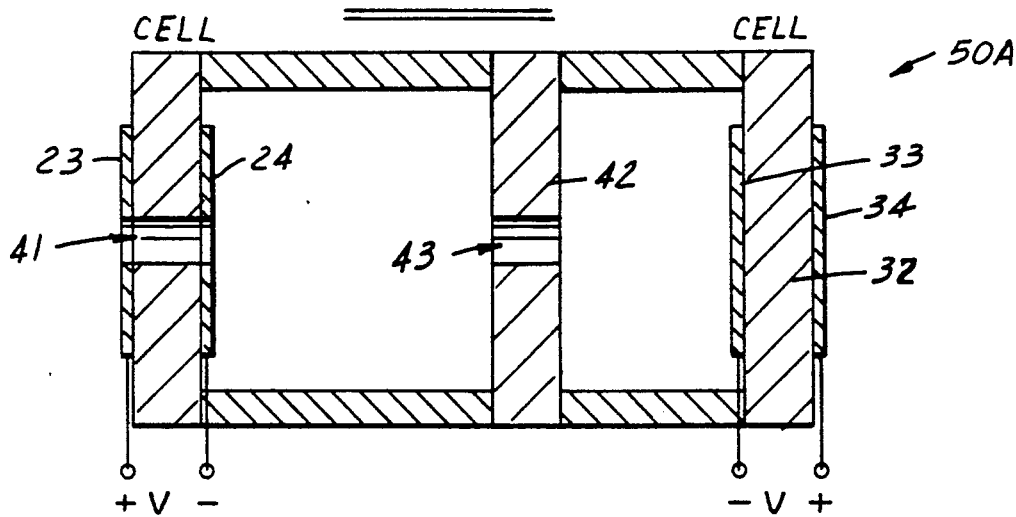
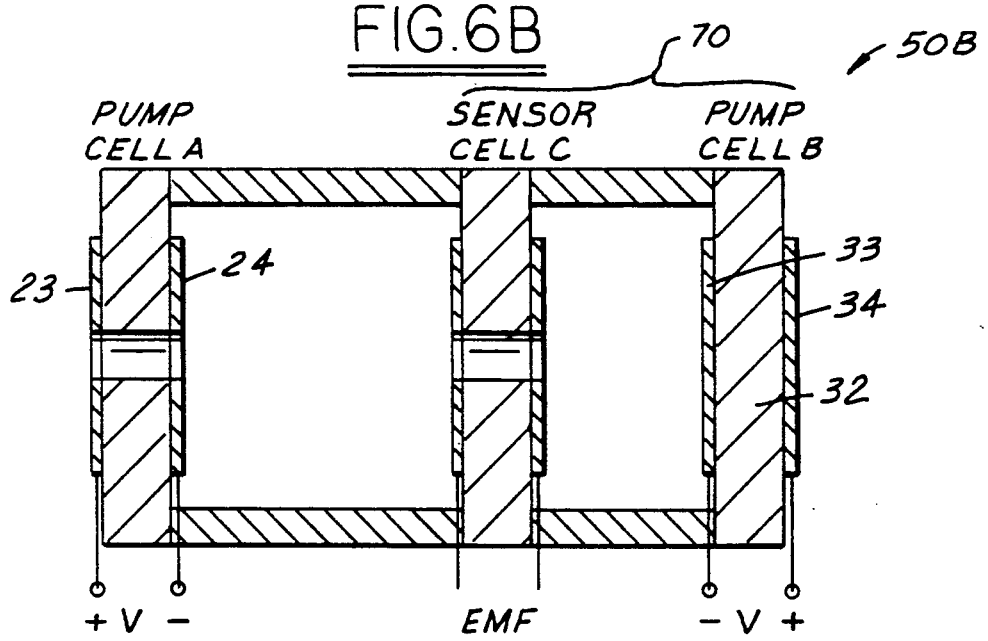
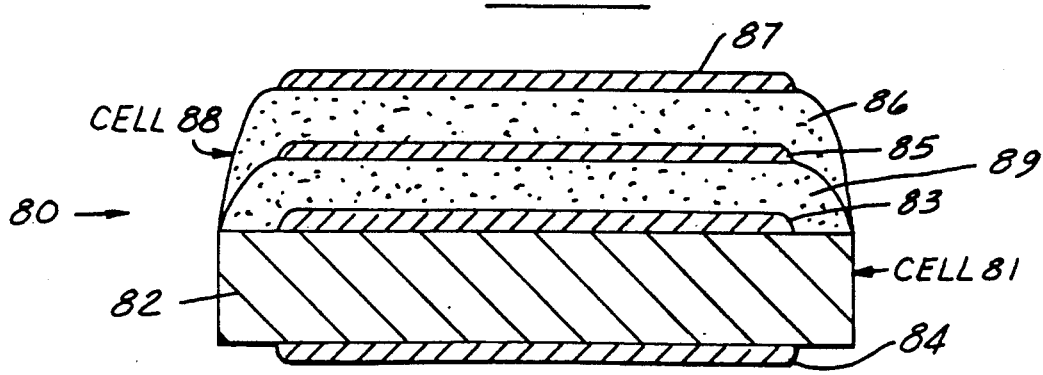

EXHAUST GAS RECIRCULATION SENSOR

BACKGROUND OF THE INVENTION

1. Field of the Invention

This invention relates to determining the amount of exhaust gas that is added to the intake air going to the cylinders of an internal combustion engine.

2. Prior Art

Exhaust gas recirculation (EGR) is commonly used in vehicles with internal combustion engines to reduce the amount of $NO_x$ produced in the engine cylinders during combustion. Depending on engine operating conditions, a certain amount of exhaust gas is added through an EGR valve to the intake air that goes to the cylinders. The dilution of the intake air charge with exhaust gas results in a lower combustion temperature and thus production of smaller amounts of $NO_x$. EGR is usually measured as percentage of exhaust gas in the combined air and exhaust intake mixture. The amount of EGR is determined by the degree of opening of the EGR valve and the difference in gas pressure across the valve. Usually, EGR is measured with a position sensor that measures the degree of opening of the EGR valve. This type of measurement is not reliable, however, because a) deposits can partially block the valve and b) changes in back pressure result in changes in the amount of EGR. Another method of determining EGR is based on the measurement of the flow of the exhaust gas added to the intake air. This is done by measuring with two pressure sensors the pressure drop across an orifice through which the recirculated exhaust gas is passed. This method of determining EGR also has problems because the orifice can be partially blocked by deposits. The present invention describes a method for measuring EGR and an EGR sensor which eliminate these problems.

SUMMARY OF THE INVENTION

This invention describes a method for measuring the percentage of EGR by measuring the percentage of $CO_2$ and $H_2O$ in the combined intake air and exhaust mixture with an electrochemical device. Correction of variable humidity in air is accomplished by measuring the percentage of $CO_2$ and $H_2O$ when the EGR valve is closed.

According to an embodiment of this invention, the electrochemical device for measuring EGR includes a first and a second $ZrO_2$ oxygen pumping cell arranged so as to define a restricted volume. This volume communicates with the ambient atmosphere (the combined intake air and exhaust gas mixture) through an aperture. In operation, a constant voltage is applied across the first cell so that the oxygen inside the restricted volume is pumped out. The value of this voltage is sufficiently high to obtain a saturation current, but less than 0.8 volts so as not to cause decomposition of any gas molecules containing oxygen. A second constant voltage is applied across the second pumping cell of sufficient magnitude (greater than 0.8 volts) to cause dissociation of all the $CO_2$ and $H_2O$ present inside the restricted volume. In this case, the saturation current of the second pumping cell is proportional to the percentage of $CO_2$ and $H_2O$ and to the percentage of EGR. According to other embodiments of this invention, the two pumping cells are more strongly decoupled by placing between them barriers to oxygen diffusion.

BRIEF DESCRIPTION OF THE DRAWINGS

FIG. 4 is a graph showing the output of the EGR sensor according to the embodiment of the present invention shown in FIG. 2 as a function of EGR.

FIG. 5 is a schematic of an electrochemical device for measuring the EGR according to a second embodiment of the present invention.

FIGS. 6A and 6B are schematics of electrochemical devices for measuring EGR in accordance with embodiments of the present invention.

FIG. 7 is a schematic of an electrochemical device having a planar configuration for measuring EGR in accordance with an embodiment of the present invention.

DETAILED DESCRIPTION OF THE INVENTION

This invention teaches a method for determining EGR based on the measurement of the amount of water vapors and carbon dioxide in the combined intake air and EGR mixture by employing an electrochemical oxygen pumping device.

Figure 1:
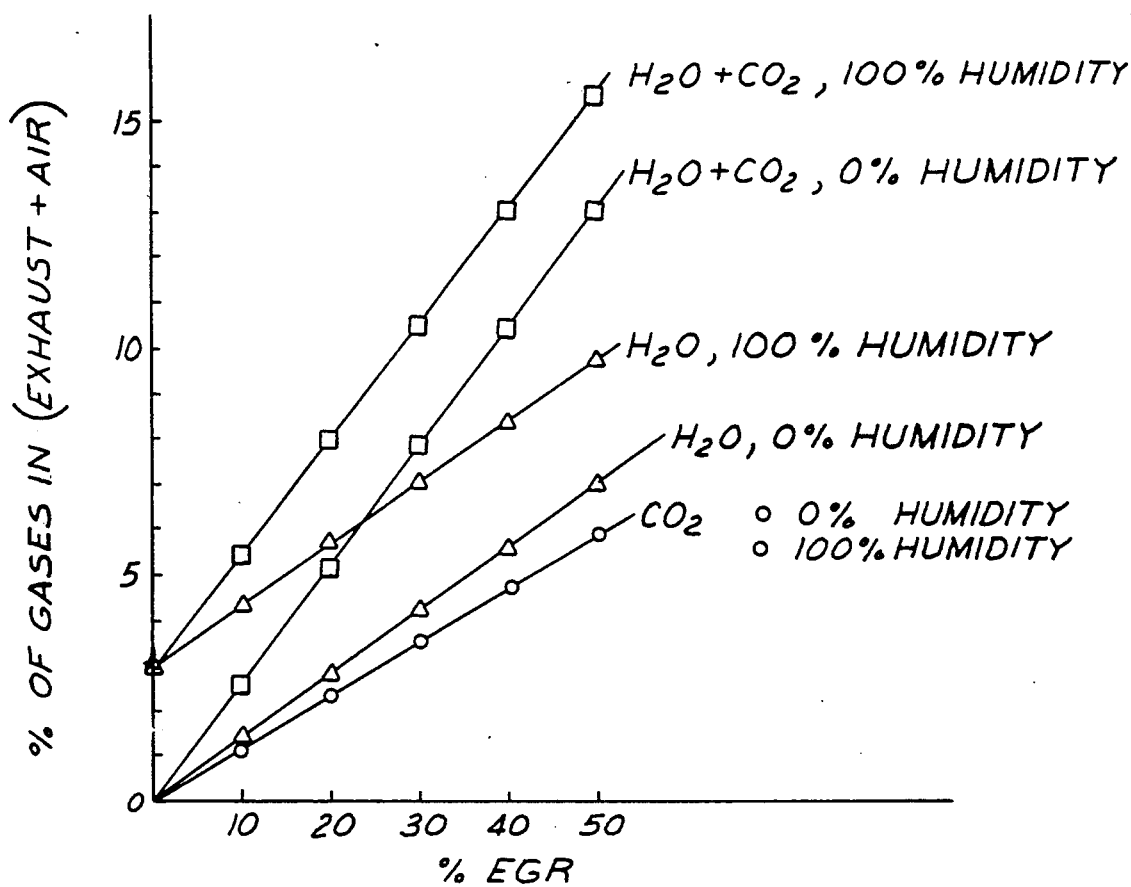
FIG. 1 is a graph relating the percentage of $CO_2$ and $H_2O$ in a combined intake air and exhaust mixture to the percentage of EGR.

For an engine controlled at the stoichiometric air-to-fuel ratio, the percentages of $CO_2$ and of $H_2O$ in the exhaust gas are constant for constant humidity in the air. For example, for a fuel with hydrogen-to-carbon ratio of 2 (stoichiometric A/F value equal to 14.7), the percentages of $CO_2$ and $H_2O$ in the exhaust gas at $A/F = 14.7$ are both equal to about 13% by volume. FIG. 1 shows the percentage of $CO_2$, $H_2O$ and ($CO_2 + H_2O$) in the combined intake air and EGR mixture as a function of the percentage of EGR. The effect of humidity in the air is indicated by showing plots for 0% and 100% humidity at a temperature of 70° F. It is apparent that the percentage of $CO_2$ is little affected by humidity and can thus be used as an accurate measure of EGR. The percentage of $H_2O$, on the other hand, depends appreciably on humidity. The error due to humidity is smaller if one measures the sum of $CO_2$ and $H_2O$. The effect of humidity can be eliminated by measuring the $H_2O$ or ($H_2O + CO_2$) for zero EGR (completely closed EGR valve).

Figure 2:
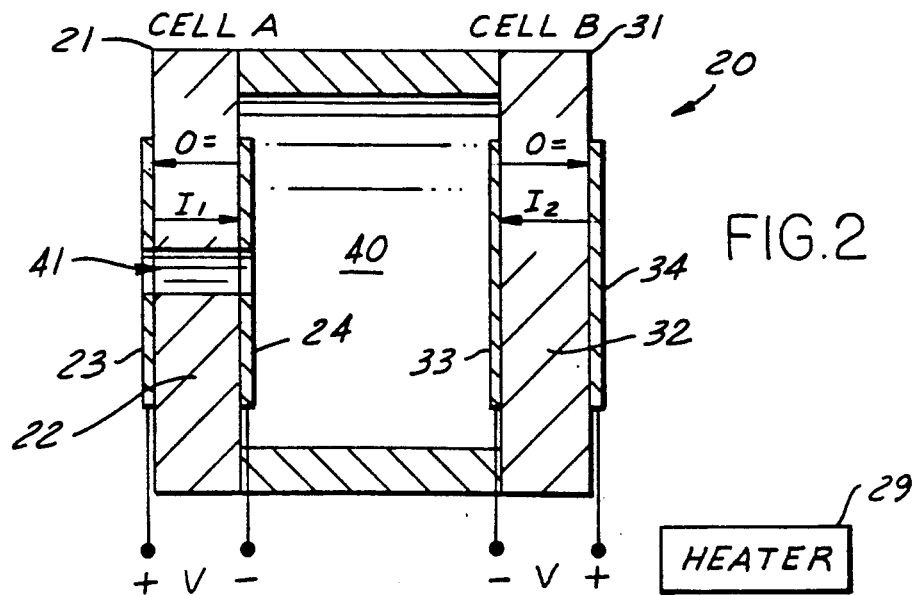
FIG. 2 is a schematic of an electrochemical device for measuring EGR according to one embodiment of this invention.

This invention measures EGR by measuring the percentage of $CO_2$ or $H_2O$ or ($CO_2 + H_2O$) in the air plus exhaust gas mixture with the sensor shown in FIG. 2. This sensor 20 has two electrochemical cells 21 and 31 arranged so that a restricted volume 40 is defined. Volume 40 is linked to the ambient atmosphere (air plus EGR) through an aperture 41 or a collection of apertures. Each of the two cells consists of a platelet (22, 32) made from an oxygen conducting solid electrolyte such as $ZrO_2$, and two electrodes (23, 24; 33, 34) applied on the two sides of the platelets. These electrodes are made from platinum or some other material according to procedures well established in the area of oxygen sensors. Electrochemical cells 21 and 31 are operated as oxygen pumps by passing currents $I_1$ and $I_2$ through them. Advantageously, a heater 29 is positioned adjacent sensor 20 to provide an elevated temperature of about at least 500° C. suitable for operation of sensor 20.

Figure 3A:
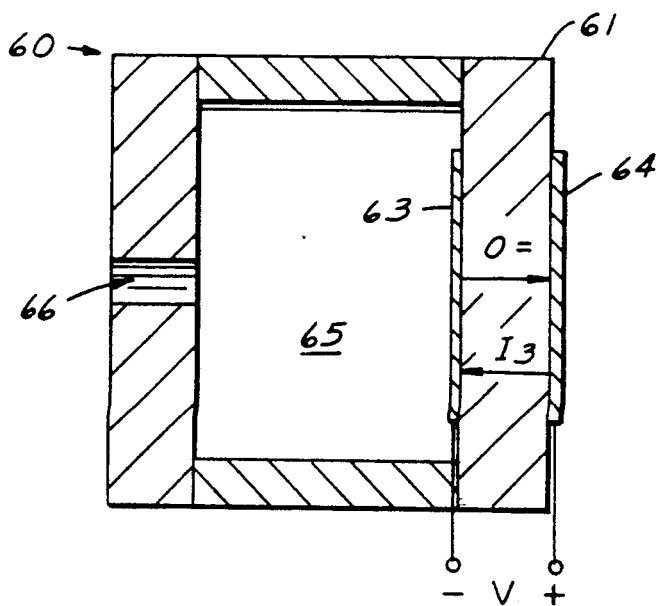
FIG. 3A is a schematic of a single-cell oxygen pumping device according to the prior art.

In order to understand the operation of device 20, first consider a single $ZrO_2$ device 60 of FIG. 3A which is a lean $O_2$-sensor based on oxygen pumping. It has a single $ZrO_2$ cell 61 made from a $ZrO_2$ platelet with two platinum electrodes 63 and 64 arranged in a structure so that a volume 65 is defined. Volume 65 communicates with the ambient gas through an aperture 66. When a voltage is applied across cell 61 so that electrode 63 is negative, a current $I_3$ passes through the $ZrO_2$ material as a result of motion of oxygen ions from electrode 63 to electrode 64.

The depletion of oxygen ions at electrode 63 is eliminated by an electrochemical reaction at this electrode which involves the dissociation of $O_2$ molecules from the gas phase and reaction with electrons of the platinum electrode to form O ions. The excess of oxygen ions at electrode 64 is eliminated by an inverse electrochemical reaction which releases $O_2$ molecules into the ambient gas. The net effect of the current through the cell is to pump $O_2$ out of volume 65. Because of the lower concentration of $O_2$ inside volume 65, there will be a diffusional flux of $O_2$ from the ambient (intake air plus exhaust gas mixture) into volume 65 through aperture 66. Under steady state conditions, the diffusional flux of $O_2$ into volume 65 will be equal to the flux of $O_2$ pumped out of volume 65 by the pumping current.

Figure 3B:
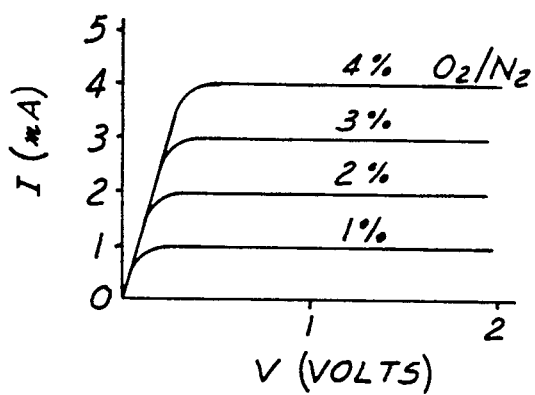
FIG. 3B is a graph showing the relation between the pumping current and the pumping voltage of the oxygen pumping device of FIG. 3A in $O_2/N_2$ gas mixtures.
Figure 3C:
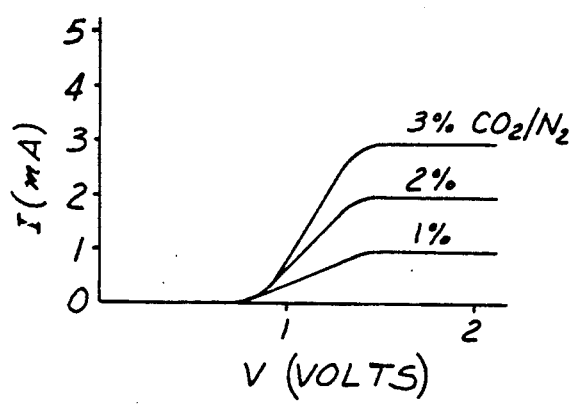
FIG. 3C is a graph showing the relation between the pumping current and the pumping voltage of the oxygen pumping device of FIG. 3A in $CO_2/N_2$ gas mixtures.
Figure 3D:
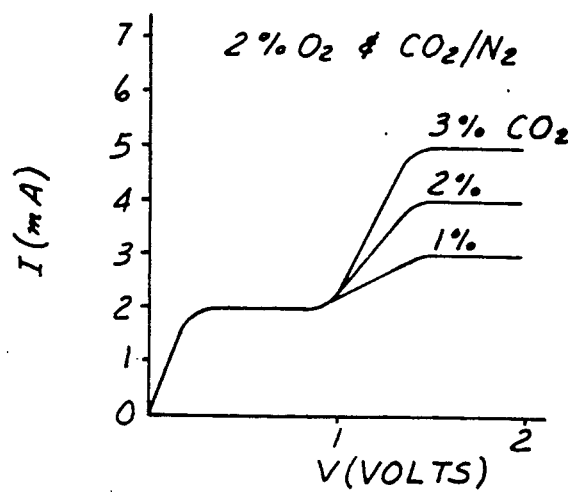
FIG. 3D is a graph showing the relation between the pumping current and the pumping voltage of the oxygen pumping device of FIG. 3A in $O_2/CO_2/N_2$ gas mixtures.

In an $O_2/N_2$ mixture, the current voltage (I-V) characteristic of device 60 is shown in FIG. 3B. For small voltages, the current increases with voltage as more oxygen is pumped out of volume 65. For sufficiently large voltages, the pumping current saturates. This corresponds to the condition that all oxygen inside volume 65 is pumped out by the current. The saturation current $I_s$ is proportional to the percentage of $O_2$ in the ambient. FIG. 3C shows the I-V characteristic of sensor 61 in a $CO_2/N_2$ mixture. Because of the lack of oxygen, the pumping current is zero for low voltages. Above a threshold value of about 0.7 volts, the pumping current increases with voltage due to electrodissociation of $CO_2$. For still higher voltages, saturation currents are again observed corresponding to the dissociation of all $CO_2$ inside volume 65. The saturation current is proportional to the percentage of $CO_2$ in the gas. A similar I-V characteristic is obtained with $H_2O/N_2$ mixtures except that the threshold voltage for the dissociation of $H_2O$ is somewhat larger (about 1.1 volt). FIG. 3D shows the I-V characteristic of device 60 in $O_2/CO_2/N_2$ gas mixtures. It is apparent that the device of FIG. 3A can be used as a $CO_2$ or $H_2O$ sensor by applying a sufficiently large voltage to achieve complete dissociation of $CO_2$ or of $H_2O$. The saturation current $I_s$ is proportional to the concentration of $CO_2$ plus $H_2O$ in the mixture.

Device 61 of FIG. 3A cannot be used for the measurement of EGR because a large and variable amount of $O_2$ also exists in the intake air plus EGR gas mixture. The measurement of EGR can be accomplished, however, with device 20 of FIG. 2. A constant voltage of less than 0.8 volts, and advantageously in the range of 0.2 to 0.8 volts, is applied across cell 21 so that electrode 24 is negative to pump all $O_2$ out of volume 40. A second constant voltage larger than 0.8 volts, and advantageously in the range of 1.1 to 2.0 volts is applied across cell 31 so that electrode 33 is negative to dissociate all $CO_2$ and $H_2O$ inside volume 40. In order to achieve current saturation in cell 31, a voltage considerably larger than 0.8 volts (e.g. 1.5 volts) is required, which means that $CO_2$ and $H_2O$ may not be measured separately. FIG. 4 shows the output (pumping current of cell 31) of sensor 20 as a function of EGR.

The device of FIG. 2 operates under the assumption that cell 21 can pump all oxygen entering volume 40 through aperture 41 so that only $CO_2$ and $H_2O$ reach cell 31. If this is not the case with the configuration of FIG. 2, the desired condition can be accomplished by modifying the device structure 50 as shown in FIG. 5. In this structure, a porous layer 38 is deposited on top of the inner electrode of cell 31. This porous layer is made from $ZrO_2$ or an inert material (e.g. spinel or aluminum oxide) and acts as a barrier to $O_2$ diffusion so that all $O_2$ is pumped out by cell 21.

Several other device configurations are possible. For example, the porous layer in the device of FIG. 5 may be replaced with a "wall" 42 having an aperture 43 as shown in device 50A of FIG. 6A. Another type of configuration is shown in device 50B of FIG. 6B. Device 50B uses a pump cell to remove the $O_2$ and a pump cell/sensor cell structure 70 (similar to the sensor structure described in U.S. Pat. No. 4,272,329 by Hetrick et al) to measure $CO_2$ plus $H_2O$.

The electrochemical device for the measurement of EGR disclosed here can also be made in a planar configuration. FIG. 7 shows one embodiment of a planar device 80 according to this invention. One starts with a dense $ZrO_2$ platelet 82 and deposits porous platinum electrodes 83 and 84 on both sides of platelet 82 to form pump cell 81. A porous layer 89 made of $ZrO_2$ or an inert material (e.g. spinel) is deposited on top of platinum electrode 83 to form a barrier to diffusion of $O_2$ molecules. A porous platinum electrode 85 is deposited on layer 89 followed by another porous layer of $ZrO_2$ 86. Finally, a porous platinum electrode 87 is deposited on top of layer 86. Porous $ZrO_2$ layer 86 and platinum electrodes 85 and 87 form pump cell 88. As in the case of the device of FIG. 2, a voltage of less than 0.8 volts is applied across pump cell 88 to pump all oxygen out of the porous parts of the structure, and a voltage of more than 1.0 volt is applied across pump cell 81 to completely decompose the $CO_2$ and $H_2O$ inside the porous layer 89. The saturation current of pump cell 81 is proportional to the percentage of EGR.

Various modifications and variations will no doubt occur to those skilled in the art to which this invention pertains. For example, the particular construction of the two cell oxygen pumping device may be varied from that disclosed herein. These and all other variations which basically rely on the teachings through which this invention has advanced the art are properly considered within the scope of this invention.

We claim:

1. An electrochemical device for measuring the percentage of exhaust gas recirculation in a combined intake air and exhaust gas mixture of an internal combustion engine, said electrochemical device including:

a first solid electrochemical pump cell having a first pair of opposing electrodes;

a second solid electrochemical pump cell having a second pair of opposing electrodes;

a supporting structure coupled to said first and second pump cells to form a restricted volume;

an aperture for providing communication between said restricted volume and an ambient of said combined intake air and exhaust gas mixture;

a first external circuit means coupled to said first pump cell to apply a constant voltage across said first pump cell so that of said first pair of opposing electrodes a first pump cell electrode inside said volume is biased negatively causing all oxygen molecules inside said volume to be pumped out by a current flowing through said first pump cell;

a second external circuit means coupled to said second pump cell to apply a constant voltage across said second pump cell so that of said second pair of opposing electrodes a second pump cell electrode inside said volume is biased negatively causing dissociation of all $CO_2$ and $H_2O$ molecules inside said volume;

a third external circuit means coupled to said second pump cell to measure a current flowing through said second pump cell, said second pump cell current being proportional to the percentage of $CO_2$ plus $H_2O$ inside said volume and also proportional to the percentage of $CO_2$ plus $H_2O$ in the combined intake air and exhaust gas mixture; and a one piece integral wall inside said volume, said wall dividing said volume into two compartments which communicate with each other through an aperture in said wall, each of said two compartments being adjacent to only one pump cell and said wall being free of electrodes.

* * * * *